United States Patent
Stites et al.

(10) Patent No.: US 7,884,253 B2
(45) Date of Patent: Feb. 8, 2011

(54) METHODS AND APPARATUS FOR SELECTIVELY PRODUCING ETHANOL FROM SYNTHESIS GAS

(75) Inventors: Ronald C. Stites, Brighton, CO (US); Jerrod Hohman, Superior, CO (US)

(73) Assignee: Range Fuels, Inc., Broomfield, CO (US)

( * ) Notice: Subject to any disclaimer, the term of this patent is extended or adjusted under 35 U.S.C. 154(b) by 0 days.

(21) Appl. No.: 12/546,976

(22) Filed: Aug. 25, 2009

(65) Prior Publication Data

US 2009/0318573 A1     Dec. 24, 2009

Related U.S. Application Data

(60) Provisional application No. 61/121,659, filed on Dec. 11, 2008, provisional application No. 61/156,917, filed on Mar. 3, 2009.

(51) Int. Cl.
*C07C 29/14* (2006.01)
*C07C 27/04* (2006.01)

(52) U.S. Cl. .................. 568/880; 568/881; 568/884; 568/885

(58) Field of Classification Search ............ None
See application file for complete search history.

(56) References Cited

U.S. PATENT DOCUMENTS

| 6,863,878 | B2 | 3/2005 | Klepper |
| 2007/0161717 | A1 | 7/2007 | Hu et al. |
| 2007/0270511 | A1 | 11/2007 | Melnichuk et al. |
| 2008/0026443 | A1 | 1/2008 | Offerman et al. |
| 2008/0058203 | A1 | 3/2008 | Iordache-Cazana et al. |
| 2009/0221725 | A1 | 9/2009 | Chornet et al. |

FOREIGN PATENT DOCUMENTS

| EP | 2072492 | 6/2009 |
| GB | 2162172 | 1/1986 |
| KR | 1019910000435 | 1/1991 |
| WO | 1983003409 | 10/1983 |
| WO | 2006123158 | 11/2006 |
| WO | 2009063173 | 5/2009 |
| WO | 2009063174 | 5/2009 |
| WO | 2009063176 | 5/2009 |

OTHER PUBLICATIONS

Pavel Afansiev et al., "Synthesis of MoSx (5 > x > 6) Amorphous Sulfides and Their Use for Preparation of MoS2 Monodispersed Microspheres", Chem. Mater., vol. 14, pp. 2826-2830 (2002).
American Coalition for Ethanol, www.ethanol.org, Dec. 25, 2006.
Clarence D. Chang, Hydrocarbons From Methanol, Marcel Dekker, Inc., Ch. 6 (pp. 75-103) 1983.
Pio Forzatti et al., "Higher Alcohol Synthesis", Catalysis Reviews, 33:1, 109-168 (Feb. 1, 1991).
J. Gauthier-Lafaye et al., Methanol and Carbonylation, Rhone-Poulenc Recherches, 1987.
Charles L. Thomas, Catalytic Processes and Proven Catalysts, Academic Press, Ch. 13 Sect. 5 and Ch. 15, Sects. 1, 2 and 4 (pp. 136-138 and 152-154) 1970.
C.L. Winter, "Make Ethanol Via Syngas", Hydrocarbon Processing, vol. 65, Issue 4, pp. 71-73 (Apr. 1986).

*Primary Examiner*—Brian J Davis
(74) *Attorney, Agent, or Firm*—O'Connor & Company; Ryan P. O'Connor

(57) ABSTRACT

The invention provides methods and apparatus for selectively producing ethanol from syngas. As disclosed herein, syngas derived from cellulosic biomass (or other sources) can be catalytically converted into methanol, which in turn can be catalytically converted into acetic acid or acetates. Finally, the acetic acid or acetates can be reduced to ethanol according to several variations. In some embodiments, yields of ethanol from biomass can exceed 100 gallons per dry ton of biomass.

30 Claims, 6 Drawing Sheets

US 7,884,253 B2

METHODS AND APPARATUS FOR SELECTIVELY PRODUCING ETHANOL FROM SYNTHESIS GAS

PRIORITY DATA

This patent application claims priority under 35 U.S.C. §120 from U.S. Provisional Patent Application Nos. 61/121,659 (filed Dec. 11, 2008) and 61/156,917 (filed Mar. 3, 2009), each for "Methods and Apparatus for Selectively Producing Ethanol from Synthesis Gas." Patent App. Nos. 61/121,659 and 61/156,917 are both incorporated by reference herein for all purposes.

FIELD OF THE INVENTION

The present invention generally relates to the field of processes for the chemical conversion of synthesis gas to alcohols, especially ethanol.

BACKGROUND OF THE INVENTION

Synthesis gas (hereinafter referred to as syngas) is a mixture of hydrogen ($H_2$) and carbon monoxide (CO). Syngas can be produced, in principle, from virtually any material containing carbon. Carbonaceous materials commonly include fossil resources such as natural gas, petroleum, coal, and lignite; and renewable resources such as lignocellulosic biomass and various carbon-rich waste materials.

There exist a variety of conversion technologies to turn these feedstocks into syngas. Conversion approaches can utilize a combination of one or more steps comprising gasification, pyrolysis, steam reforming, and/or partial oxidation of a carbon-containing feedstock.

Syngas is a platform intermediate in the chemical and biorefining industries and has a vast number of uses. Syngas can be converted into alkanes, olefins, oxygenates, and alcohols. These chemicals can be blended into, or used directly as, diesel fuel, gasoline, and other liquid fuels. Syngas can also be directly combusted to produce heat and power.

Today, almost half of all gasoline sold in the United States contains ethanol (American Coalition for Ethanol, www.ethanol.org, 2006). The ethanol in gasoline and other liquid fuels raises both the oxygen and the octane content of the fuels, allowing them to burn more efficiently and produce fewer toxic emissions.

It is preferable to utilize a renewable resource to produce ethanol because of the rising economic, environmental, and social costs associated with fossil resources. Calculations show that when renewable feedstocks, such as biomass, are converted into syngas using techniques described above, a selective process for converting this syngas into ethanol has the theoretical potential to produce approximately 200 gallons of ethanol per ton of biomass. No publicly known process, however, can achieve such yields of ethanol.

In light of the state of the art, what is needed is a method, as well as an apparatus to carry out the method, to improve the selectivity and yield to ethanol. Specifically, there exists a need to overcome the carbon loss to methanol, propanol, and higher alcohols, when ethanol is desired. Additionally, a need exists to reduce the carbon loss to the water-gas shift reaction that consumes CO and generates $CO_2$.

SUMMARY OF THE INVENTION

The present invention addresses the commercial need in the art by providing methods and apparatus to generate high yields of ethanol from syngas.

In some variations, the invention provides a method for producing ethanol from biomass, the method comprising:
(i) converting the biomass into a first stream comprising syngas;
(ii) catalytically converting at least some of the syngas into a second stream comprising methanol;
(iii) separating some of the syngas into hydrogen and carbon monoxide;
(iv) catalytically converting at least some of the methanol with some of the carbon monoxide into a third stream comprising acetic acid; and
(v) reducing at least some of the acetic acid with some of the hydrogen into a fourth stream comprising ethanol.

In some embodiments, the reducing step is catalyzed by a Mo/Co/S catalyst. This Mo/Co/S catalyst can further comprise an alkali promoter.

In preferred embodiments, ethanol is produced at a yield of at least 75 gallons per dry ton of the biomass, such as at least 100 gallons per dry ton of the biomass.

In other variations of the invention, a method if provided for producing ethanol from biomass, the method comprising:
(i) converting the biomass into a first stream comprising syngas;
(ii) catalytically converting at least some of the syngas into a second stream comprising methanol;
(iii) catalytically converting at least some of the methanol with CO into a third stream comprising acetic acid, wherein $H_2$ is further introduced, thereby generating acetaldehyde; and
(iv) reducing at least some of the acetic acid and the acetaldehyde with $H_2$ into a fourth stream comprising ethanol.

In some embodiments, the reducing step is catalyzed by a Mo/Co/S catalyst. This Mo/Co/S catalyst can further comprise an alkali promoter.

In preferred embodiments, ethanol is produced at a yield of at least 75 gallons per dry ton of the biomass, such as at least 100 gallons per dry ton of the biomass.

In still other variations of the invention, a method is provided for producing ethanol from biomass, the method comprising:
(i) converting the biomass into a first stream comprising syngas;
(ii) catalytically converting at least some of the syngas into a second stream comprising methanol;
(iii) catalytically converting at least some of the methanol with CO into a third stream comprising acetic acid;
(iv) esterifying the acetic acid with ethanol to generate ethyl acetate;
(v) reducing at least some of the ethyl acetate with $H_2$ into a fourth stream comprising ethanol; and
(vi) optionally recycling the ethanol produced in step (v) back to step (iv).

In some embodiments, the reducing step is catalyzed by a Mo/Co/S catalyst. This Mo/Co/S catalyst can further comprise an alkali promoter.

In preferred embodiments, ethanol is produced at a yield of at least 75 gallons per dry ton of the biomass, such as at least 100 gallons per dry ton of the biomass.

In yet other variations of the invention, a method is provided for producing ethanol from biomass, the method comprising:
(i) converting the biomass into a first stream comprising syngas;
(ii) catalytically converting at least some of the syngas into a second stream comprising methanol;
(iii) catalytically converting at least some of the methanol with CO into a third stream comprising acetic acid;

(iv) esterifying the acetic acid with an alcohol to generate an acetate;

(v) reducing at least some of the acetate with $H_2$ into a fourth stream comprising ethanol;

(vi) separating the fourth stream into an ethanol stream and a recovered-alcohol stream; and (vii) recycling the recovered-alcohol stream from step (vi) back to step (iv).

In some embodiments, the alcohol in step (iv) is methanol, ethanol, or a combination of methanol and ethanol. In some embodiments, the alcohol in step (iv) is selected from $C_1$-$C_{10}$ alcohols, such as $C_3$-$C_6$ alcohols. For example, the alcohol can be selected from the group consisting of propanol, butanol, pentanol, hexanol, heptanol, hexanol, cylcohexanol, phenol, and combinations thereof.

In some variations, this invention provides a method for producing ethanol from syngas, the method comprising:

(i) in a first reactor, catalytically converting at least some of the syngas into methanol;

(ii) in a second reactor, catalytically converting at least some of the methanol into acetic acid;

(iii) feeding a portion of the acetic acid into the first reactor, under conditions effective for esterification of acetic acid with the methanol, thereby generating an acetate; and (iv) reducing at least some of the acetate with $H_2$ to generate ethanol.

In some embodiments, a portion of the syngas is separated to produce a $H_2$-containing stream for the reducing step. In some embodiments, a portion of the syngas is separated to produce a CO-containing stream, followed by feeding at least some of the CO-containing stream into the second reactor.

In the first reactor, acetic acid can be converted to ethanol. Also in the first reactor, ethyl acetate can be converted to ethanol. Some embodiments include esterification of acetic acid with ethanol in the first reactor to generate ethyl acetate.

Certain embodiments include feeding recycled or stored methanol to the first reactor. Some embodiments include feeding recycled or stored acetic acid to the first reactor.

Preferably, ethanol is produced at a carbon-atom selectivity of at least 70%, such as at least 80% carbon-atom selectivity to ethanol.

DETAILED DESCRIPTION OF EMBODIMENTS OF THE INVENTION

Figure 1:
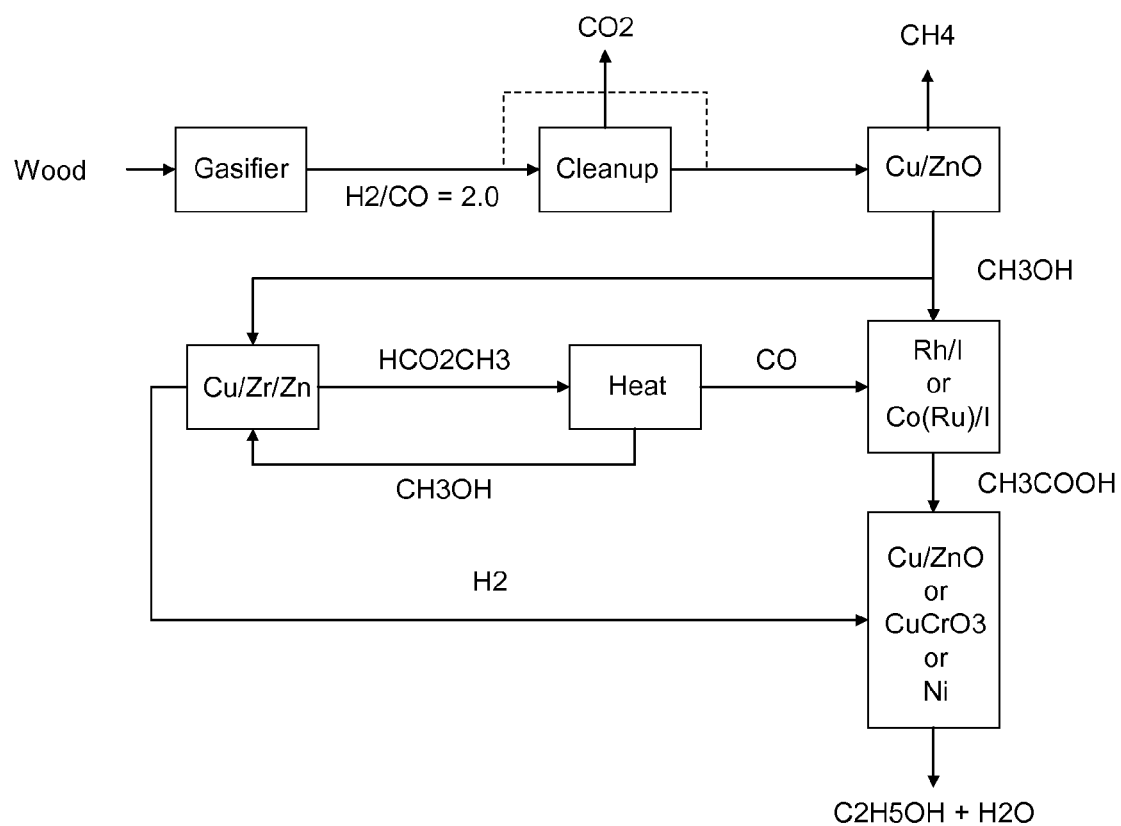
FIG. 1 is a process block-flow diagram depicting some embodiments of the invention, for selective ethanol production from biomass.

This description will enable one skilled in the art to make and use the invention, and it describes several embodiments, adaptations, variations, alternatives, and uses of the invention, including what is presently believed to be the best mode of carrying out the invention.

As used in this specification and the appended claims, the singular forms "a," "an," and "the" include plural referents unless the context clearly indicates otherwise. Unless defined otherwise, all technical and scientific terms used herein have the same meaning as is commonly understood by one of ordinary skill in the art to which this invention belongs.

Unless otherwise indicated, all numbers expressing reaction conditions, stoichiometries, concentrations of components, and so forth used in the specification and claims are to be understood as being modified in all instances by the term "about." Accordingly, unless indicated to the contrary, the numerical parameters set forth in the following specification and attached claims are approximations that may vary depending at least upon the specific analytical technique. Any numerical value inherently contains certain errors necessarily resulting from the standard deviation found in its respective testing measurements.

The present invention will now be described by reference to the following detailed description and accompanying figures which characterize and illustrate some preferred embodiments for producing ethanol. This description by no means limits the scope and spirit of the present invention.

The methods and systems of the invention can accommodate a wide range of feedstocks of various types, sizes, and moisture contents. Any carbon-containing compound can be used as a feed material for the production of syngas. For example, biomass such as agricultural wastes, forest products, grasses, and other cellulosic material can be used. In some embodiments, the feedstock includes one or more materials selected from timber harvesting residues, softwood chips, hardwood chips, tree branches, tree stumps, leaves, bark, sawdust, off-spec paper pulp, corn, corn stover, wheat straw, rice straw, sugarcane bagasse, switchgrass, miscanthus, animal manure, municipal garbage, municipal sewage, commercial waste, grape pumice, almond shells, pecan shells, coconut shells, coffee grounds, grass pellets, hay pellets, wood pellets, cardboard, paper, plastic, and cloth. A person of ordinary skill in the art will appreciate that the feedstock options are virtually unlimited.

Some variations of this invention teach producing methanol using commercially available Cu/ZnO catalysts, converting the methanol to acetic acid, and reducing the acetic acid to ethanol. Some variations proceed via methyl acetate, ethyl acetate, or heavier acetates as intermediates. Many variations and embodiments are contemplated, and there will typically be trade-offs between the most-selective paths and less-selective paths that can be more cost-effective and/or practical.

In some variations, the invention provides a method comprising four distinct steps, as will now be summarized and then further described.

1. Cellulose to Syngas $$C_6(H_2O)_5 + H_2O \rightarrow 6CO + 6H_2$$

2. Syngas to Methanol $$CO + 2H_2 \rightarrow CH_3OH$$

3. Methanol to Acetic Acid $$CH_3OH + CO \rightarrow CH_3COOH$$

4. Acetic Acid to Ethanol $$CH_3COOH + 2H_2 \rightarrow C_2H_5OH + H_2O$$

Step 1 is a non-limiting generalization of the conversion of cellulosic materials, represented by $C_6(H_2O)_5$, into a gas stream comprising syngas. This step can be carried out according to methods described in Klepper, U.S. Pat. No. 6,863,878, for example. In some embodiments, syngas is provided according to methods described in Klepper et al., "Methods and apparatus for producing syngas," U.S. patent application Ser. No. 12/166,167 (filed Jul. 1, 2008). U.S. patent application Ser. No. 12/166,167 is hereby incorporated by reference herein in its entirety.

Step 2 is the well-known methanol-synthesis reaction from syngas. As will be recognized by a person of ordinary skill in the art, there are a number of commercial catalysts available to conduct this reaction, such as Cu/ZnO, Cu/Zn/Al, and others. This reaction can be highly selective, such as 80%, 90%, 95%, or higher selectivity to methanol, depending on temperature, pressure, recycle, and other conditions.

Step 3, wherein methanol is converted to acetic acid, is also a well-known commercial process. Several catalysts and process configurations are available industrially. For example, a common method is the "Monsanto Process" which employs a rhodium iodide catalyst and can be highly selective, such as 90%, 95%, 99%, or higher selectivity to acetic acid.

Step 4 represents the conversion of the acetic acid obtained in step 3 to ethanol. This step can utilize a Mo/Co/S/alkali catalyst, in some embodiments (e.g., see the Example below). The reaction can be selective towards ethanol, such as at least 50%, 60%, 70%, 80%, 90%, 95%, or higher selectivity to ethanol, depending at least on temperature, pressure, and other reaction conditions. Preferred embodiments of step 4 are at least 90% selective to ethanol.

During the conversion of syngas to alcohols over certain catalysts, the mechanism for chain growth is believed to involve organic acids as intermediates. A likely mechanism for chain growth is the insertion of CO into the C—O bond of an alcohol.

Without being limited by any particular hypothesis, it is believed that under certain conditions an adsorbed acid is reduced to the corresponding normal alcohol, which may progress via the relatively well-known base-catalyzed reduction of C=O bonds by sulfides. The strongly reducing Mo/Co/S/alkali catalyst may be involved either directly or indirectly. The metals may react directly in their reduced state or they may release sulfur—as $H_2S$ or some other reactive sulfur species—to accomplish the reduction. Upon reduction, a C=O group is replaced by a $CH_2$ group. Some embodiments of the present invention favor this reduction reaction while minimizing the carbonylation reaction.

In order to favor the reduction reaction, it can be beneficial to (a) reduce CO concentration, (b) increase the Co/Mo ratio, (c) increase $H_2$ and/or $H_2S$ concentrations, (d) increase the basicity of the catalysts by using basic supports, and/or (e) reduce the reaction temperature. Option (a) can slow down the carbonylation reaction, for example. Options (b) and (c) can increase the reduction reactivity, for example. Option (d) can improve reaction rate, for example. With respect to option (e), it will be recognized that the equilibrium constant for the reduction reaction is higher at lower temperatures. At temperatures less than about 300° C., acetic acid reduction to ethanol can become the dominant reaction.

Reactions represented by steps 2, 3, and 4 are all exothermic and thermodynamically favored by lower temperatures and higher pressures. In some embodiments, optimal operating conditions for all of these reactions are similar (e.g., about 200-300° C. and 1000-3000 psig), which is convenient from a process design standpoint.

A reactor is any apparatus capable of being effective for converting reactants to products. A reactor can be a single vessel or a plurality of vessels in various arrangements. For example, in some variations, the reactor comprises a large number of tubes filled with one or more catalysts. A reactor can be engineered and operated in a wide variety of ways. The reactor operation can be continuous, semicontinuous, or batch. Operation that is substantially continuous and at steady state is preferable. The flow pattern can be substantially plug flow, substantially well-mixed, or a flow pattern between these extremes. The flow direction can be vertical-upflow, vertical-downflow, or horizontal. A vertical configuration can be preferable.

A reactor can contain at least one catalyst composition that tends to catalyze the conversion of reactants to products. The catalyst phase can be a packed bed or a fluidized bed. The catalyst particles can be sized and configured such that the chemistry is, in some embodiments, mass-transfer-limited or kinetically limited. The catalyst can take the form of a powder, pellets, granules, beads, extrudates, and so on. When a catalyst support is optionally employed, the support may assume any physical form such as pellets, spheres, monolithic channels, etc. The supports may be coprecipitated with active metal species; or the support may be treated with the catalytic metal species and then used as is or formed into the aforementioned shapes; or the support may be formed into the aforementioned shapes and then treated with the catalytic species.

In some embodiments, steps 2-4 are conducted in the same reactor. In other embodiments, steps 2, 3, and 4 are all conducted in separate reactor units or in different zones of a single physical reactor unit.

In some embodiments, conditions effective for step 2 include a feed hydrogen-carbon monoxide molar ratio ($H_2$/CO) from about 0.2-4.0, preferably about 0.5-2.0, and more preferably about 0.5-1.5. These ratios are indicative of certain embodiments and are not limiting. It is possible to operate at feed $H_2$/CO ratios less than 0.2 as well as greater than 4, including 5, 10, or even higher. It is known that high $H_2$/CO ratios can be obtained with extensive steam reforming and/or water-gas shift in operations prior to the syngas-to-alcohol reactor.

In some embodiments, conditions effective for steps 2, 3, and 4 include reactor temperatures from about 200-400° C., preferably about 250-350° C. Depending on the catalyst chosen, changes to reactor temperature can change conversions, selectivities, and catalyst stability. As is recognized in the art, increasing temperatures can sometimes be used to compensate for reduced catalyst activity over long operating times. While higher temperatures can increase rates, lower temperatures can be preferred thermodynamically.

Preferably, the syngas entering step 2 is compressed. Conditions effective for producing alcohols from syngas include reactor pressures from about 20-500 atm, preferably about 50-200 atm or higher. Generally, productivity increases with increasing reactor pressure, and pressures outside of these ranges can be employed with varying effectiveness.

In some embodiments, conditions effective for step 2 includes average reactor residence times from about 0.1-10 seconds, preferably about 0.5-2 seconds. "Average reactor residence time" is the mean of the residence-time distribution of the reactor contents under actual operating conditions. Catalyst contact times can also be calculated by a skilled artisan and these times will typically also be in the range of 0.1-10 seconds, although it will be appreciated that it is certainly possible to operate at shorter or longer times.

Certain variations of this invention will now be further described by reference to the figures, which are intended not to limit the invention but rather to illustrate exemplary process embodiments.

In FIG. 1, a process block-flow diagram is depicted. The process involves gasification (using known methods) and water-gas shift to $H_2/CO=2.0$ (for example), followed by clean-up and removal of excess $CO_2$. A small amount of $CO_2$ can be allowed to slip through clean-up to improve methanol synthesis over the Cu/ZnO catalyst. The Cu/ZnO catalyst can be operated a temperature of about 240° C. and pressure as low as 400 psig.

Gasification of wood (an exemplary biomass feedstock) can produce considerable amounts of $CH_4$ (typically about 10-20%). Methane production can be adjusted by varying the operating temperature. Higher temperature lowers the $CH_4$ content, but at a cost of energy and reformer longevity. The operating pressure is preferably raised in order to assist in the rejection of $CH_4$. By operating the Cu/ZnO catalyst at higher pressure, up to 2500 psig, the reaction can be driven to a high mole fraction of $CH_4$ in the tail gas. The tail gas made in this way should have relatively high fuel value without additional clean-up.

A portion of the methanol stream is sent to the acetic acid synthesis step, wherein methanol combines with carbon monoxide to generate acetic acid. One exemplary process is the Monsanto process using rhodium and iodide in a stirred reactor. This process can be over 98% selective to acetic acid, operating at, for example, 200° C. and 1000 psig. Purified CO is preferably used, although an inert diluent could be added. The CO needed for this step can be CO generated from gasification, or by other means recited below.

Another exemplary process for converting methanol to acetic acid is the BP process, employing iridium along with iodide. Yet another variation employs cobalt and iodide (a commercial BASF process) or cobalt/ruthenium and iodide. The use of cobalt generally necessitates higher pressures (such as 5000 psig), optionally with the addition of a controlled amount of $H_2$.

In some variations, CO can be derived, at least in part, from methanol as follows. One can react 2 moles of methanol over a Cu/Zr/Zn catalyst to make 1 mole of methyl formate and 2 moles of $H_2$. The methyl formate can be thermally decomposed to CO and 1 mole of methanol which can be recycled. This variation provides two independent gas streams. One is high purity CO and the other high purity $H_2$. The amounts of these gases produced, from a stoichiometric standpoint (two moles $H_2$ and one mole CO), are suitable to carry out both carbonylation of methanol to acetic acid and subsequent reduction of the acetic acid to ethanol and water.

Figure 2:
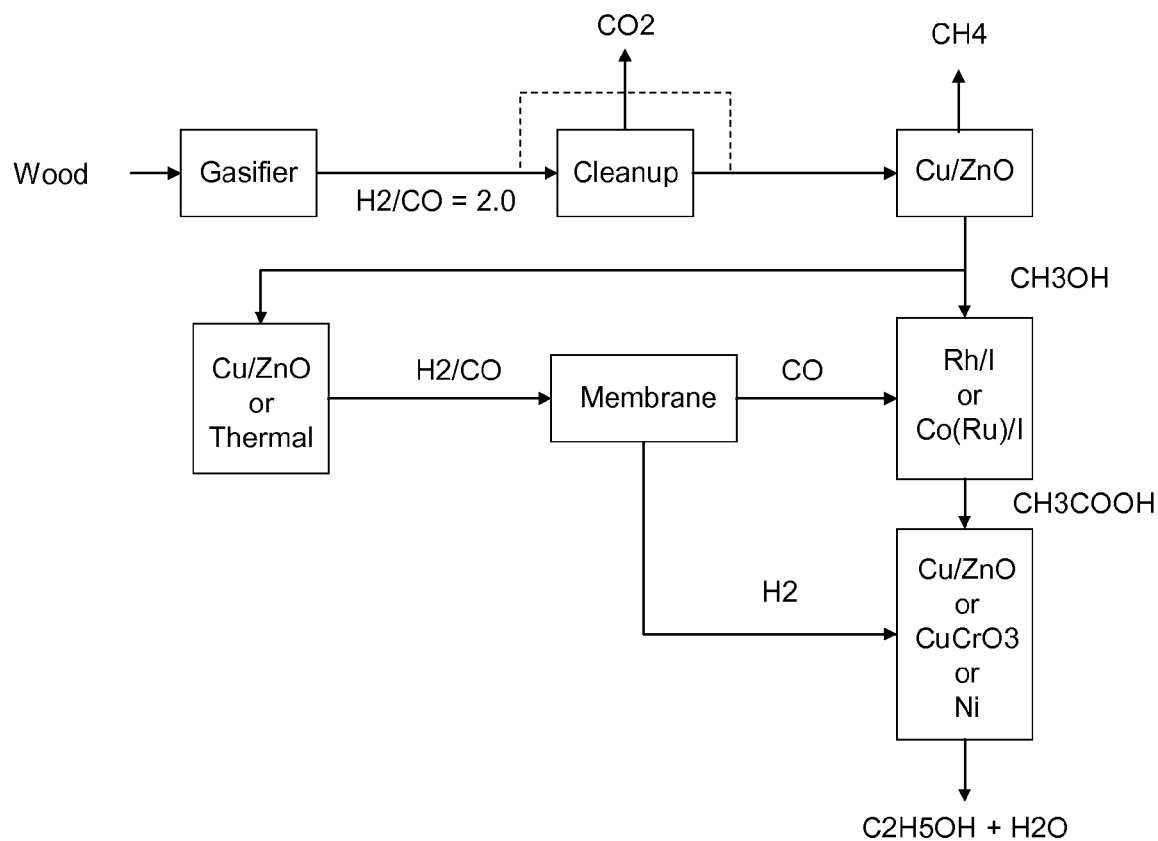
FIG. 2 is a process block-flow diagram depicting certain embodiments of the invention, for selective ethanol production from biomass.

Other methods for making a mix of syngas from methanol are shown in FIG. 2. These options include simple thermal cracking as well as reaction of the methanol over Cu/ZnO (reverse of the synthesis reaction). The product will generally be a mix of gases that will have to be separated using, for example, membranes.

Figure 3:
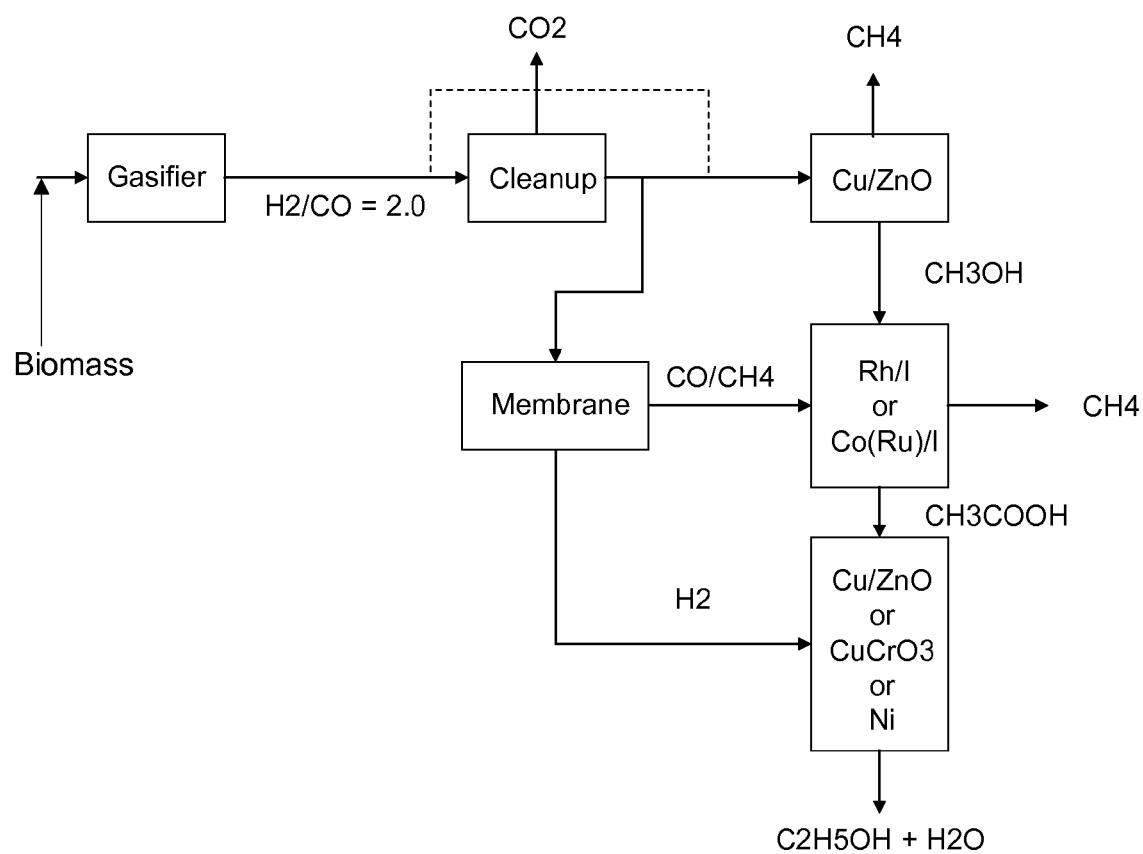
FIG. 3 is a process block-flow diagram depicting embodiments of the invention, for selective ethanol production from biomass.

In FIG. 3, syngas is provided from gasification, and gas separation is employed to provide the CO needed for the acetic acid formation step, and to provide the $H_2$ needed for the ethanol formation step. Methane rejection is shown as part of the methanol carbonylation step (assuming methane is present in the feed to that step).

Figure 4:
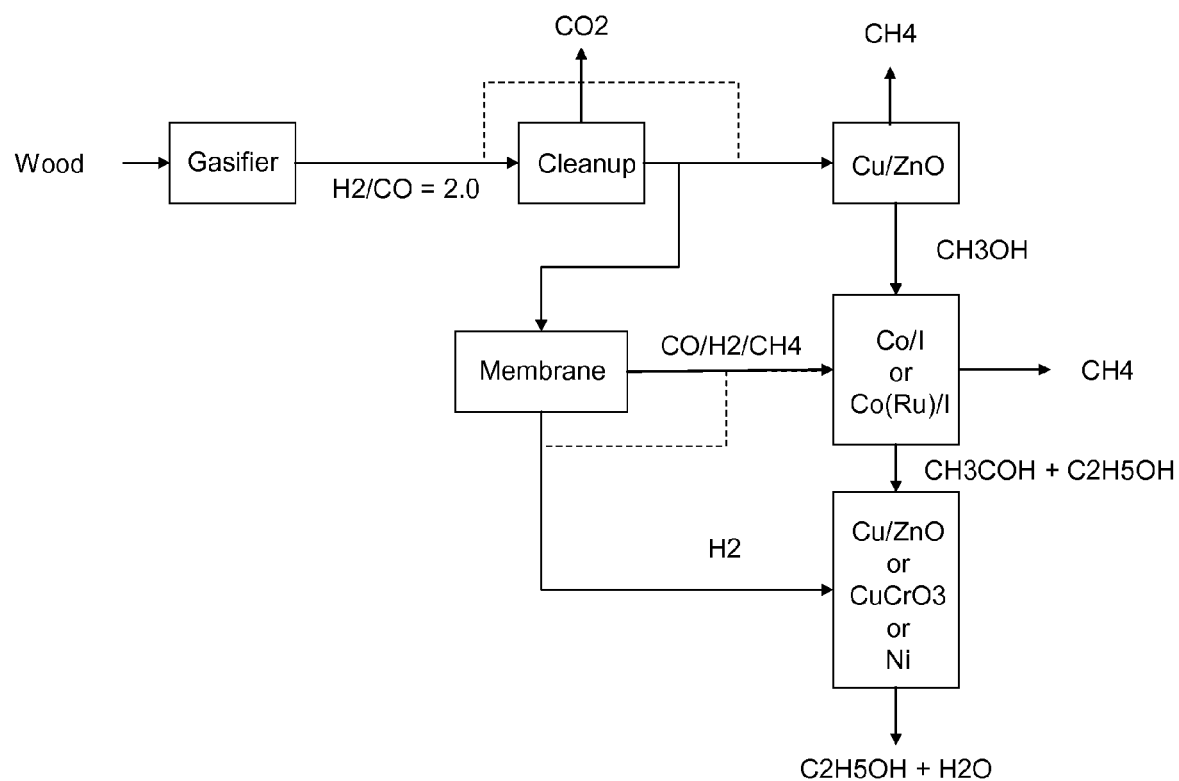
FIG. 4 is a process block-flow diagram depicting embodiments of the invention, for hydrous ethanol production from biomass.

Another variation of the carbonylation step is shown in FIG. 4. Here, $H_2$ is deliberately introduced into the carbonylation step to encourage a partial reduction of the carbonylated product. The result is a mix of acetaldehyde and ethanol. The final step in the process of FIG. 4 is the reduction of the acetic acid, or a mixture comprising acetaldehyde and ethanol, to ethanol and water using hydrogen. The final product will be a mixture of ethanol and water that can be distilled.

Figure 5:
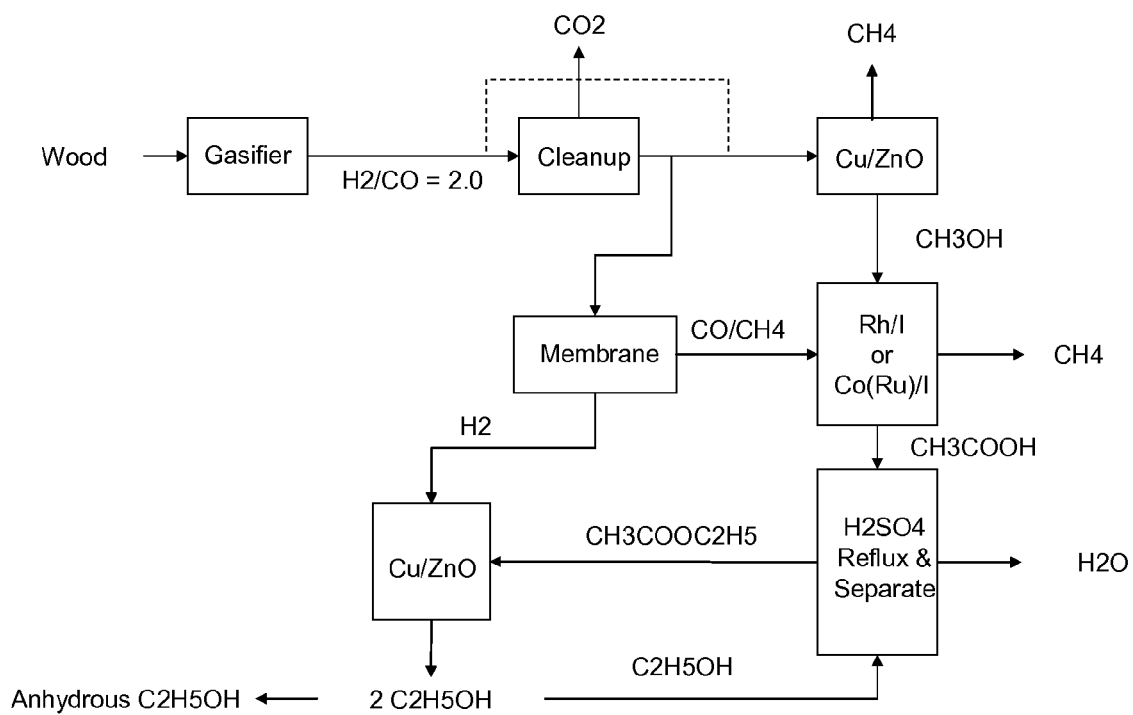
FIG. 5 is a process block-flow diagram depicting embodiments of the invention, for anhydrous ethanol production from biomass.

FIG. 5 shows a process block-flow diagram for producing anhydrous ethanol. This process uses the methyl iodide (Rh or Co) approach to make acetic acid. The acetic acid is esterified with ethanol to make ethyl acetate. Sulfuric acid reflux, or other suitable methods, can be used. This allows for separation of the water that is required as part of the overall reduction of an organic acid to an alcohol. The ethyl acetate is readily reduced to 2 moles of ethanol using hydrogen and a catalyst (e.g., Cu/ZnO). A portion of the ethanol, such as about half the ethanol, can be recycled to the esterification step to produce more ethyl acetate.

Figure 6:
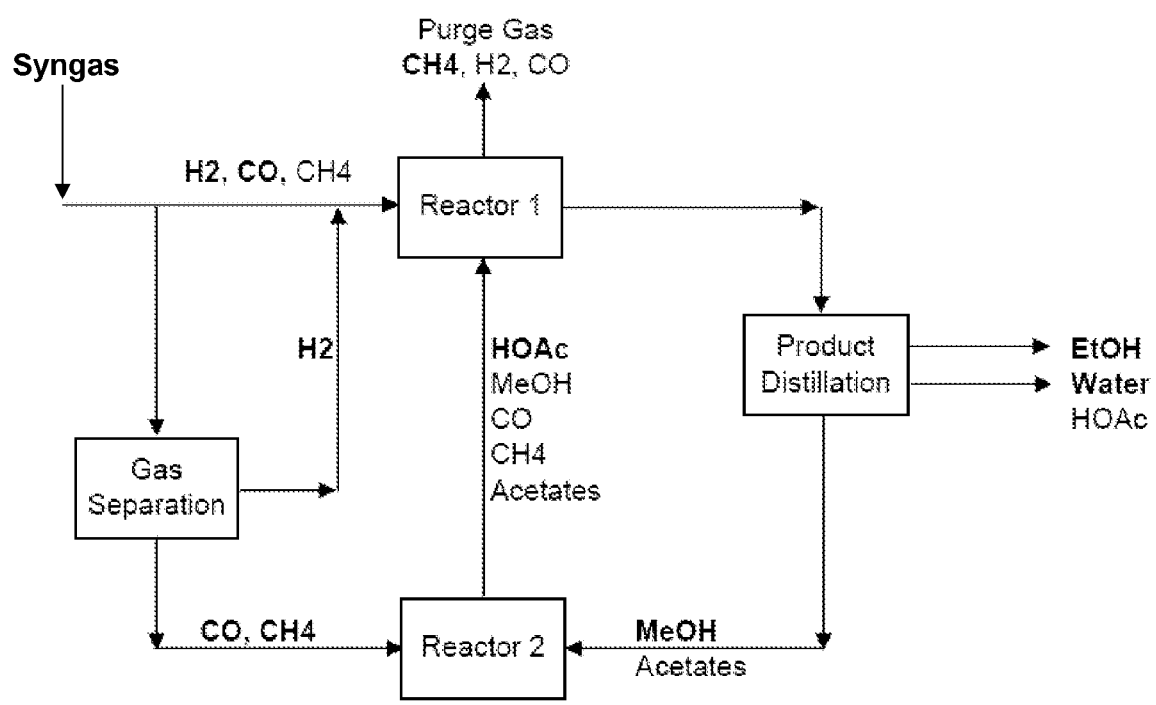
FIG. 6 is a process block-flow diagram depicting embodiments of the invention, for ethanol production from syngas.

Some variations of the invention are premised, at least in part, on the realization that a single reaction vessel can be employed for both syngas conversion to methanol as well as for esterification of the methanol (produced or recycled) with acetic acid to produce methyl acetate. FIG. 6 shows an exemplary block-flow diagram.

In these variations, syngas is converted to ethanol via a two-step process. In a first reactor, methanol ("MeOH" in FIG. 6) is produced from syngas. The methanol created in the first reactor is sent to a second reactor, wherein methanol is converted to acetic acid ("HOAc" in FIG. 6). The acetic acid (along with acetates) is routed back to the first reactor, wherein at least some of the acetic acid undergoes esterification with methanol. Also in the first reactor, the ester is reduced (with $H_2$) to produce a mixture of ethanol and esters; ethanol ("EtOH" in FIG. 6) can be recovered by any known means. Methanol and acetates can be completely recycled, or a purge stream can be withdrawn at one or more locations. Example 2 herein describes some embodiments of these variations of the invention.

Esterification of acetic acid with alcohol does not need to utilize methanol or ethanol. In some embodiments, heavier alcohols can be employed for esterification. It can be advantageous to select an alcohol based on the ease of separation (e.g., in the "Product Distillation" block of FIG. 6) and recycle. Factors that could be considered include molecular weight, boiling point or vapor pressure, and whether a specific alcohol is hydrophilic or hydrophobic. Hydrophobic alcohols (such as aromatic alcohols) are desirable, in some embodiments, to allow more-convenient separation of the acetates from ethanol/water.

Generally, alcohols can be selected from, for example, $C_1$-$C_{10}$ alcohols, such as $C_3$-$C_6$ alcohols, including linear, branched, cyclic, and aromatic alcohols and polyols. In some embodiments, one or more alcohols are selected from the group consisting of propanol, butanol, pentanol, hexanol, heptanol, hexanol, cylcohexanol, phenol, and combinations thereof.

Reaction selectivities can be calculated on a carbon-atom basis, meaning the ratio of the moles of a specific product to the total moles of all products, scaled by the number of carbon atoms in the species. This definition accounts for the mole-number change due to reaction, and best describes the fate of the carbon from converted CO.

In various embodiments of the present invention, the product(s) may be characterized by reaction selectivities, based on syngas converted, of about 50-90% or higher to ethanol. The product stream may include other non-alcohol oxygenates such as aldehydes, esters, carboxylic acids, and ketones. The yields (selectivity times conversion) according to these various embodiments can be 25-80% or higher and will depend on a large number of factors, as will be appreciated.

Other selectivity definitions are possible, such as "alcohol selectivity" which accounts for the carbon distribution within the alcohols produced. In preferred embodiments of this invention, the alcohol selectivity to ethanol is high, with low amounts of $C_{3+}$ alcohols produced. High alcohol selectivities to ethanol can be achieved, such as in excess of 85%, 95%, or even higher, due to the chemistry and process configurations of preferred processes as taught herein.

Variations of the invention can be particularly useful when high yields of ethanol from biomass are desired. In various embodiments, the ethanol yield is about 75, 100, 125 or more gallons per dry ton of biomass.

In general, the specific selection of catalyst configuration (geometry), $H_2$/CO ratio, temperature, pressure, residence time (or feed rate), and other reactor-engineering parameters will be selected for each reactor to provide an economical process. These parameters are not regarded as critical to the present invention. It is within the ordinary skill in the art to experiment with different reactor conditions to optimize selectivity to ethanol.

EXAMPLE 1

This example demonstrates an exemplary embodiment for acetic acid reduction with syngas using a Co/Mo/S/K catalyst. The catalyst is prepared such that Co and Mo are combined with an atomic ratio of Co to Mo of about 0.5. The catalyst composition also comprises sulfur, in an initial atomic ratio of S to (Co+Mo) of about 2. Potassium is introduced as $K_2CO_3$ so that the atomic ratio of K to (Co+Mo) is about 0.4. This catalyst composition is subjected to an experiment as described.

A total of 56.75 g of pelletized catalyst is loaded into a 1" outer-diameter reactor tube. The catalyst is activated for 24 hours at 280° C. and 1500 psig in a flow of 1.5:1 $H_2$:CO (molar ratio) before use. Syngas is passed over the catalyst under the following conditions, with the results in column A. Next, acetic acid is injected, using a high-pressure solvent pump and under similar conditions, with the results shown in column B.

The overall carbon closure for experiment A is 98.5% and for experiment B is 97.0%. These data demonstrate the effective conversion of acetic acid to ethanol.

|  | A | B |
|---|---|---|
| Time On Stream (total hrs) | 552 | 570 |
| Temperature (° C.) | 325 | 325 |
| Pressure (psig) | 1500 | 1500 |
| H2/CO molar ratio | 2.75 | 2.62 |
| GHSV (L/kg-cat/hr) | 6316 | 6372 |
| Recycle Ratio (L feed/L recycle) | 3.2 | 3.1 |
| CO Conversion (%) Overall | 73.9 | 72.2 |
| CO$_2$ Selectivity (%) | 15.3 | 21.7 |
| CH$_4$ Selectivity (%) | 16.5 | 14.5 |
| Liquid Injected |  |  |
| Acetic acid (g/hr) | 0.0 | 8.4 |
| Liquids Produced |  |  |
| Methanol (g/hr) | 9.60 | 8.81 |
| Ethanol (g/hr) | 4.91 | 9.43 |
| Propanol (g/hr) | 0.84 | 1.33 |
| Other Oxygenates (g/hr) | 0.10 | 0.20 |
| Acetic acid (g/hr) | Not Detected | Not Detected |
| Water (g/hr) | 2.39 | 2.97 |

EXAMPLE 2

This Example 2 employs the process configuration shown in FIG. 6. In Reactor 1, methanol is generated and acetate is reduced. The following reactions are contemplated in Reactor 1:

$$CO + 2H_2 \rightarrow CH_3OH \quad (i)$$

$$CO + H_2O \rightarrow H_2 + CO_2 \quad (ii)$$

$$CH_3COOH + CH_3OH \rightarrow CH_3COOCH_3 + H_2O \quad (iii)$$

$$CH_3COOCH_3 + CH_3CH_2OH \rightarrow CH_3COOCH_2CH_3 + CH_3OH \quad (iv)$$

$$CH_3COOCH_3 + 2H_2 \rightarrow CH_3CH_2OH + CH_3OH \quad (v)$$

Reactions (i)-(iv) are equilibrium-limited. Reaction (v) operates at about 85% (±5%) conversion of methyl acetate.

In Reactor 2, methanol is converted to acetic acid according to:

$$CH_3OH + CO \rightarrow CH_3COOH \quad (vi)$$

Reaction (vi) operates at about 98% conversion of methanol.

Syngas is fed to a gas-separation unit, from which substantially all of the hydrogen and about half of the methane and carbon monoxide is fed to Reactor 1. Products from Reactor 1 are cooled and the gases are recycled (at a recycle ratio of about 3) along with a purge stream.

The liquid products are separated with the separation being substantially controlled between methanol and ethanol. Some of the ethyl acetate and most of the acetic acid remains in the ethanol product stream. Additional CO, $CH_4$, and equilibrium amounts of the acetates and alcohols are lost as distillation off-gas. The methanol and acetates are fed to Reactor 2 along with the second half of the CO+$CH_4$ split. The entire product stream from Reactor 2 is fed to Reactor 1. Acetic acid is removed from the ethanol stream and is optionally recycled back to the process (e.g., input to Reactor 1).

The following table summarizes the conversion and selectivity data predicted by an integrated process simulation in this Example 2.

|  | (lbmol/hr) | Conversion (conv/fed) | Selectivity (mol/mol rxd) |
|---|---|---|---|
| CO Converted | 30.43 | 97.4% |  |
| CO$_2$ Produced | 4.77 |  | 15.7% |
| Methyl Acetate Produced | 0.53 |  | 5.2% |
| Methanol Produced | 0.50 |  | 1.6% |
| Ethyl Acetate Produced | 0.85 |  | 11.2% |
| Ethanol Produced | 9.72 |  | 63.9% |
| Acetic Acid Produced | 0.47 |  | 3.1% |

EXAMPLE 3

Example 3 relates to the variation shown in FIG. 5. In this experiment, ethyl acetate is injected as a liquid into a plug-flow reactor packed with a commercial Cu/ZnO/$Al_2O_3$ methanol-synthesis catalyst (MK-121, Haldor Topsoe). The ethyl acetate is reduced to high-purity ethanol using a flow of 96 vol % $H_2$ (with 4 vol % Ar as a tracer) under the following conditions: pressure=650 psig; temperature=220° C.; and GHSV (vol/vol)=14,500/hr.

Approximately 87% of the ethyl acetate is reduced to ethanol in a single pass. Approximately 96% of the ethyl acetate is accounted for. Small amounts of methane and methanol are noted. The composition of the resulting product is 87.9 wt % ethanol, 10.9 wt % ethyl acetate, and 1.1 wt % methanol on a dry basis. The product also contains a small amount of water (about 0.3 wt %).

EXAMPLE 4

Example 4 relates to the variation shown in FIG. 6. In this experiment, it is shown that methanol and methyl acetate can be simultaneously formed and at least partially reduced to the desired ethanol product over a $Cu/ZnO/Al_2O_3$ catalyst (MK-121, Haldor Topsoe). Syngas and acetic acid are introduced to this methanol-synthesis catalyst under the following conditions: pressure=650 psig; temperature=260° C.; and GHSV (vol/vol)=21,700/hr. The composition of the syngas fed is 62 vol % $H_2$, 31 vol % CO, 3% $CO_2$, and 4% Ar.

With a single reactor pass, about 54% of the acetic acid is converted to ethanol and 87% of the acetic acid is converted either to ethanol or to acetates that can be reduced by $H_2$ to ethanol. Approximately 90% of the acetates can be accounted for. The measured composition of the resulting product includes approximately 29.3% ethanol, 24.0% methanol, 21.6% acetic acid, 18.3% methyl acetate, and 5.8% ethyl acetate on a dry weight basis. About 13 wt % water is also detected in the product stream.

EXAMPLE 5

In this Example 5, it is experimentally demonstrated that heavier alcohols can be used to simultaneously esterify and reduce acetic acid to ethanol. One advantage of this variation is that product separation can be more effective. Both acetic acid and 1-propanol are introduced into a plug-flow reactor packed with a $Cu/ZnO/Al_2O_3$ catalyst (MK-121, Haldor Topsoe) under the following conditions: pressure=650 psig; temperature=240° C.; GHSV (vol/vol)=14,500/hr; 96 vol % $H_2$; and 4 vol % Ar.

With a single reactor pass, approximately 88% of the acetic acid is converted to other products with 66% of the acetic acid being converted directly to ethanol. The liquid product contains the heavy alcohol (1-propanol) and the associated acetate ester. The liquid product using 1-propanol as the heavy alcohol includes, on a dry weight basis, about 39.2% 1-propanol, 33.6% ethanol, 14.1% propyl acetate, 8.8% acetic acid, 3.8% ethyl acetate, and 0.3% methanol. About 16 wt % water is also detected in the product stream.

In this detailed description, reference has been made to multiple embodiments of the invention and non-limiting examples relating to how the invention can be understood and practiced. Other embodiments that do not provide all of the features and advantages set forth herein may be utilized, without departing from the spirit and scope of the present invention. For example, syngas can be generated or provided by any means, not necessarily from biomass gasification. This invention incorporates routine experimentation and optimization of the methods and systems described herein.

All publications, patents, and patent applications cited in this specification are herein incorporated by reference in their entirety as if each publication, patent, or patent application were specifically and individually put forth herein.

To the extent there are variations of the invention, which are within the spirit of the disclosure or equivalent to the inventions found in the appended claims, it is the intent that this patent will cover those variations as well. The present invention shall only be limited by what is claimed.

What is claimed is:

1. A method for producing ethanol from biomass, said method comprising:
   (i) converting said biomass into a first stream comprising syngas;
   (ii) catalytically converting at least some of said syngas into a second stream comprising methanol;
   (iii) separating some of said syngas into hydrogen and carbon monoxide;
   (iv) catalytically converting at least some of said methanol with some of said carbon monoxide into a third stream comprising acetic acid; and
   (v) reducing at least some of said acetic acid with some of said hydrogen into a fourth stream comprising ethanol.

2. The method of claim 1, wherein said reducing is catalyzed by a Mo/Co/S catalyst.

3. The method of claim 2, wherein said Mo/Co/S catalyst further comprises an alkali promoter.

4. The method of claim 1, wherein ethanol is produced at a yield of at least 75 gallons per dry ton of said biomass.

5. The method of claim 4, wherein ethanol is produced at a yield of at least 100 gallons per dry ton of said biomass.

6. A method for producing ethanol from biomass, said method comprising:
   (i) converting said biomass into a first stream comprising syngas;
   (ii) catalytically converting at least some of said syngas into a second stream comprising methanol;
   (iii) catalytically converting at least some of said methanol with CO into a third stream comprising acetic acid, wherein $H_2$ is further introduced, thereby generating acetaldehyde; and
   (iv) reducing at least some of said acetic acid and said acetaldehyde with $H_2$ into a fourth stream comprising ethanol.

7. The method of claim 6, wherein said reducing is catalyzed by a Mo/Co/S catalyst.

8. The method of claim 7, wherein said Mo/Co/S catalyst further comprises an alkali promoter.

9. The method of claim 6, wherein ethanol is produced at a yield of at least 75 gallons per dry ton of said biomass.

10. The method of claim 9, wherein ethanol is produced at a yield of at least 100 gallons per dry ton of said biomass.

11. A method for producing ethanol from biomass, said method comprising:
    (i) converting said biomass into a first stream comprising syngas;
    (ii) catalytically converting at least some of said syngas into a second stream comprising methanol;
    (iii) catalytically converting at least some of said methanol with CO into a third stream comprising acetic acid;
    (iv) esterifying said acetic acid with ethanol to generate ethyl acetate;
    (v) reducing at least some of said ethyl acetate with $H_2$ into a fourth stream comprising ethanol, wherein said reducing is catalyzed by a Mo/Co/S catalyst; and
    (vi) optionally recycling said ethanol produced in step (v) back to step (iv).

12. The method of claim 11, wherein step (vi) includes recycling a portion of said ethanol produced in step (v) back to step (iv).

13. The method of claim 12, wherein said Mo/Co/S catalyst further comprises an alkali promoter.

14. The method of claim 11, wherein ethanol is produced at a yield of at least 75 gallons per dry ton of said biomass.

15. The method of claim 14, wherein ethanol is produced at a yield of at least 100 gallons per dry ton of said biomass.

16. A method for producing ethanol from biomass, said method comprising:
    (i) converting said biomass into a first stream comprising syngas;
    (ii) catalytically converting at least some of said syngas into a second stream comprising methanol;

(iii) catalytically converting at least some of said methanol with CO into a third stream comprising acetic acid;
(iv) esterifying said acetic acid with a $C_3$ or higher alcohol to generate an acetate;
(v) reducing at least some of said acetate with $H_2$ into a fourth stream comprising ethanol;
(vi) separating said fourth stream into an ethanol stream and a recovered-alcohol stream, wherein said recovered alcohol stream comprises said $C_3$ or higher alcohol; and
(vii) recycling said recovered-alcohol stream from step (vi) back to step (iv).

17. The method of claim 16, wherein said $C_3$ or higher alcohol in step (iv) is selected from $C_3$-$C_{10}$ alcohols.

18. The method of claim 17, wherein said $C_3$ or higher alcohol is selected from $C_3$-$C_6$ alcohols.

19. The method of claim 17, wherein said $C_3$ or higher alcohol is selected from the group consisting of propanol, butanol, pentanol, hexanol, heptanol, hexanol, cylcohexanol, phenol, and combinations thereof.

20. A method for producing ethanol from syngas, said method comprising:
(i) in a first reactor, catalytically converting at least some of said syngas into methanol;
(ii) in a second reactor, catalytically converting at least some of said methanol into acetic acid;
(iii) feeding a portion of said acetic acid into said first reactor, under conditions effective for esterification of acetic acid with said methanol, thereby generating an acetate; and
(iv) reducing at least some of said acetate with $H_2$ to generate ethanol.

21. The method of claim 20, wherein a portion of said syngas is separated to produce a $H_2$-containing stream for said reducing step.

22. The method of claim 20, wherein a portion of said syngas is separated to produce a CO-containing stream, and further comprising feeding at least some of said CO-containing stream into said second reactor.

23. The method of claim 20, wherein in said first reactor, acetic acid is converted to ethanol.

24. The method of claim 20, wherein in said first reactor, said acetate is converted to ethanol.

25. The method of claim 20, further comprising esterification of acetic acid with ethanol in said first reactor to generate ethyl acetate.

26. The method of claim 20, further comprising feeding recycled or stored methanol to said first reactor.

27. The method of claim 20, further comprising feeding recycled or stored acetic acid to said first reactor.

28. The method of claim 20, wherein ethanol is produced at a carbon-atom selectivity of at least 70%.

29. The method of claim 28, wherein ethanol is produced at a carbon-atom selectivity of at least 80%.

30. A method for producing ethanol from biomass, said method comprising:
(i) converting said biomass into a first stream comprising syngas;
(ii) catalytically converting at least some of said syngas into a second stream comprising methanol;
(iii) catalytically converting at least some of said methanol with CO into a third stream comprising acetic acid;
(iv) esterifying said acetic acid with methanol to generate methyl acetate;
(v) reducing at least some of said methyl acetate with $H_2$ into a fourth stream comprising methanol and ethanol, wherein said reducing is catalyzed by a Mo/Co/S catalyst; and
(vi) optionally recycling a portion of said methanol produced in step (v) back to step (iv).

* * * * *